United States Patent
Epstein

[19]

[11] Patent Number: 6,098,319
[45] Date of Patent: *Aug. 8, 2000

[54] BALANCING APPLIANCE FOR FOOTWEAR ITEM

[76] Inventor: Merel Epstein, 27895 Berrywood La., Farmington Hills, Mich. 48334

[ * ] Notice: This patent issued on a continued prosecution application filed under 37 CFR 1.53(d), and is subject to the twenty year patent term provisions of 35 U.S.C. 154(a)(2).

[21] Appl. No.: 09/096,946

[22] Filed: Jun. 12, 1998

Related U.S. Application Data

[60] Provisional application No. 60/058,828, Sep. 15, 1997.

[51] Int. Cl.⁷ .................................................. A61F 5/14
[52] U.S. Cl. .................................. 36/159; 36/155; 36/43; 36/71
[58] Field of Search ........................... 36/140–144, 155, 36/159, 43, 44, 71, 37, 81, 85, 173, 174, 176, 178, 180

[56] References Cited

U.S. PATENT DOCUMENTS

| | | | |
|---|---|---|---|
| 492,994 | 3/1893 | Sawyer | 36/71 |
| 879,527 | 2/1908 | Dorrity | 36/71 |
| 1,762,025 | 6/1930 | Marks | 36/180 |
| 1,958,097 | 5/1934 | Shaw | 36/144 |
| 2,055,072 | 9/1936 | Everston | 36/178 |
| 2,096,500 | 10/1937 | McCahan et al. | 36/144 |
| 2,749,628 | 6/1956 | Morder | 36/141 |
| 3,071,877 | 1/1963 | Stickles | 36/140 |
| 3,099,267 | 7/1963 | Cherniak | 36/174 |
| 3,417,494 | 12/1968 | Claff | 36/71 |
| 3,984,926 | 10/1976 | Calderon | 36/71 |
| 4,510,700 | 4/1985 | Brown | 36/44 |
| 4,530,173 | 7/1985 | Jesinsky, Jr. | 36/81 |
| 4,760,655 | 8/1988 | Mauch | 36/44 |
| 4,800,657 | 1/1989 | Brown | 36/44 |
| 4,879,821 | 11/1989 | Graham et al. | 36/44 |
| 5,068,983 | 12/1991 | Marc | 36/44 |
| 5,170,572 | 12/1992 | Kantro | 36/43 |
| 5,345,701 | 9/1994 | Smith | 36/144 |
| 5,695,850 | 12/1997 | Crow | 36/44 |
| 5,746,011 | 5/1998 | Hedstrom | 36/140 |

FOREIGN PATENT DOCUMENTS

| | | | |
|---|---|---|---|
| 091013561 | 9/1991 | WIPO | 36/141 |

*Primary Examiner*—Paul T. Sewell
*Assistant Examiner*—J. Mohandesi
*Attorney, Agent, or Firm*—Plunkett & Cooney, P.C.

[57] ABSTRACT

A balancing disc or appliance for use in with a shoe insole, or biomechanical device, such as an ankle or foot brace, for balancing the gait of a user is defined by a substantially circular disc or body element having a top surface and a bottom surface. The top surface and the bottom surface are angularly inclined with respect to each other in an angle ranging from about 2° to about 6°. Optimally, an adhesive is deposited onto one of the surfaces for facilitating affixation of the disc to an insole or similar orthotic device. The disc is, preferably, formed from a flexible material. Since the device is substantially circular in nature, it may be rotated about a vertical axis through a 360° arc to facilitate minute adjustments in the balance of the user.

2 Claims, 1 Drawing Sheet

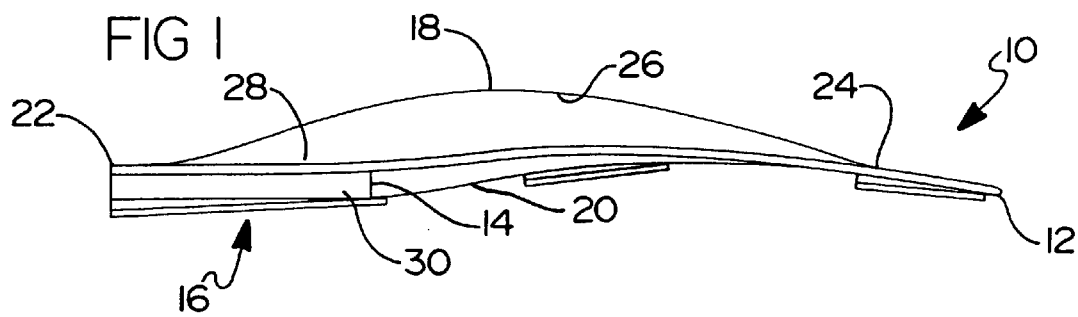
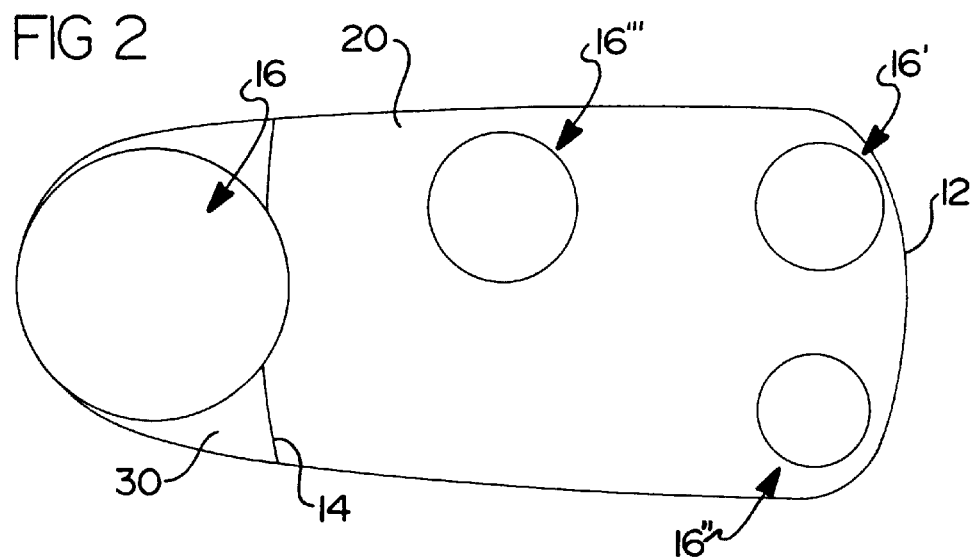
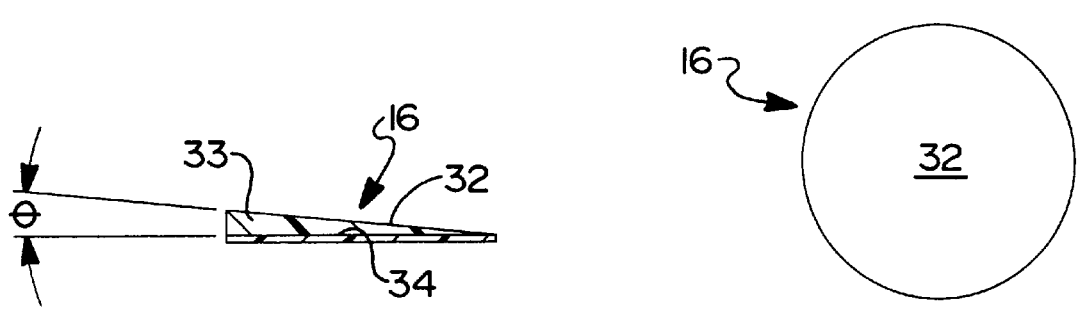

BALANCING APPLIANCE FOR FOOTWEAR ITEM

CROSS-REFERENCE TO RELATED APPLICATIONS

This application is a completion application based upon co-pending U.S. provisional patent application Ser. No. 60/058,828, filed Sep. 15, 1997 for "BALANCING DISC FOR AN ORTHOTIC FOOT DEVICE," the disclosure of which is hereby incorporated by reference.

STATEMENT REGARDING FEDERALLY FUNDED RESEARCH

Not Applicable.

BACKGROUND OF THE INVENTION

1. Field of the Invention

The present invention involves the field of foot devices. Even more particularly, the present invention involves the field of orthotic foot devices used in chiropracty, physical therapy, orthopedics, osteopathy, and general health care. More particularly, the present invention concerns a balancing disc for use with shoes or orthotic foot devices.

2. Prior Art

Orthotic foot devices, or "orthotics", are used as inserts into footwear to give a user enhanced biomechanical balance and weight distribution during both standing and ambulation. Orthotic foot devices may be either medically prescribed to a precise configuration or an "off the shelf" item which are emplaced within a shoe or other footwear items. Typically, such orthotics comprise a plate in the shape of a plantar part of a human foot plus optional additions, such as wedges, which are secured to the plate, anterior or posterior or both, to create proper alignment and balance of skeletal and muscular body components, thereby providing enhanced balance and weight distribution to the user.

Heretofore, in practice, once installed in a footwear item in attempting to effect proper balance and weight distribution, a skilled technician or practitioner usually would make adjustments to either or both the posterior and anterior areas of the orthotic devices by emplacement of wedges in correct orientation. This is a time consuming task, because of the minute corrections necessary to be made. It is to be, thus, appreciated that there has not been a simple and convenient way for making these necessary adjustments.

The present invention, as detailed below, provides a universal device appliance or balancing disc for providing balance and weight distribution adjustment which is easily integrated with existing orthotic foot devices as well as into other footwear items or devices. In accordance herewith, there is provided a wedge-shaped circular disc, which is particularly adapted to be securable to an orthotic plate in a plurality of incremental orientations through a 360° arc in both the posterior and anterior portions of the orthotic device to provide the requisite adjustment for effecting proper balance and weight distribution. Similarly, the present appliance may be used in conjunction with insoles or be directly attached to a footwear item such as a shoe, sandal, etc.

SUMMARY OF THE INVENTION

The present balancing disc for an orthotic foot device which generally comprises:

a substantially circular member having a top surface and a bottom surface, the surfaces being angularly inclined with respect to each other.

The balancing disc hereof has its top surface and bottom surface angularly inclined with respect to each other by an angle $\emptyset$. The angle $\emptyset$ will, generally, range from about 2° to about 6°.

The angular inclination enables compensation for balance, depending upon a user's foot.

Ordinarily, the disc hereof is placed upon a heel portion of an orthotic device, such as an insole, but may be placed directly over the heel or other portion of a shoe or in another position on the orthotic device.

Also, a plurality of the devices hereof may be disposed about an insole at appropriate positions.

The present device may be made from any suitable material, such as a flexible rubber, synthetic resinous material or the like.

Additionally, an adhesive may be deposited onto the top surface of the disc to facilitate the securement thereof to the insole or shoe.

Also, from a commercial standpoint, a plurality of these disc's may be packaged as a kit with the plurality having various angles of inclination between the top and bottom surafaces thereof.

For a more complete understanding of the present invention, reference is made to the following detailed description and accompanying drawing. In the drawing, like reference characters refer to like parts throughout the several views, in which:

BRIEF DESCRIPTION OF THE DRAWING

FIG. 1 is a side view of an orthotic foot device deploying the balancing disc of the present invention;

FIG. 2 is a bottom view of the orthotic foot device of FIG. 1 with the disc in place;

FIG. 3 is a side view of the disc hereof; and

FIG. 4 is a top plan view of the disc hereof.

DETAILED DESCRIPTION OF THE EMBODIMENTS

With more particularity, and with reference to the drawing, there is depicted an orthotic foot device or orthotic device, generally, denoted at 10 having a balancing disc of the present invention secured thereto and which is, generally, denoted at 16.

In a preferred utilization hereof, the present invention is used with either an extrinsically posted heel cup orthotic device or a flat heel cup orthotic device. Both the flat heel cup type and posted heel cup type of devices are well-known and commercially available, one source being sold under the trademark EVER-FLEX by Ever-Flex, Inc. of Lincoln Park, Mich.

Additionally, the present disc may be used intrinsically in an anterior portion or extrinsically posted orthotic device, both laterally and/or medially of either an intrinsically or extrinsically posted device. Clearly, the disc hereof may be used for both the anterior and posterior portions of the orthotic device, as needed. Likewise, the present invention may be deployed on a flat insole or may be directly emplaced within a footwear item, such as a shoe, sandal, etc.

As shown in the drawing, and with reference to the utilization of the disc hereof in conjunction with an orthotic device, and as is known to those skilled in the art to which the present invention pertains, the typical orthotic device 10 includes a plate or sole plate 12 made of a flexible rigid or semi-rigid material, such as a foam, leather, steel, plastic or the like. Herein for illustrative purposes, the orthotic device has an intrinsically posted heel cup portion depicted in the drawing. As shown, the plate 12 has a first or top or foot-engaging surface 18 and a second or bottom or footwear-engaging surface 20 opposite the first surface 18. The plate 12 and, particularly, the first surface 18 thereof is shaped to the sole of a human foot, with curvatures, as appropriate. The plate 12 comprises a posterior portion 22, an anterior portion 24, and an arch portion 26 between and connecting the posterior portion 22 and the anterior portion 24.

Clearly, the disc hereof may be used for both the anterior and posterior portions of the device, as needed.

In use, a post 14, made of any suitable rigid, flexible or semi-flexible material, as required, including synthetic rubber, foam, etc., and the like, may be secured to the second or bottom surface 20 of the plate 12 about the posterior portion 22. The post 14 has a first surface 28 and a second surface 30 opposite the first surface. The first surface 28 is shaped to snugly overlie the posterior portion 22 of the plate 12 at the second surface 20 thereof. The second surface 30 of the post 14 is, usually, substantially flat or planar. The post 14 is attached to the plate 12 at the posterior portion 18 thereof by any suitable means, such an adhesive or the like.

As noted above, heretofore, if the plate 12 and/or a combination of the plate 12 and the post 14 did not effect the desired result, minute adjustments were accomplished with rectangular-shaped shims or wedges or similar devices. The present disc 16 obviates this, as detailed below.

The disc 16 hereof is a substantially circular solid wedge member made of either rigid, semi-flexible or flexible material, such as plastic, rubber, synthetic rubber or the like, as required, prescribed and/or desired.

The disc 16 has a first surface 32, a second surface 34, opposite the first surface 32, and a side wall 33 integrally formed with the first surface 32 and the second surface 34. The first surface 32 and the second surface 34 are each substantially circular planar surfaces. The first surface 32 is angularly inclined with respect to the second surface 34 by an angle θ, which generally ranges from about 2° to about 6°. Thus, the disc 16 defines a circular wedge or shim.

The first surface 32 of the disc 16 may be attached to either the post 14 or the plate 12, or both, by any suitable means, such as an adhesive or the like. Because the disc 16 is circular, it may be universally rotated through a 360° arc, to provide the minute adjustments prerequisite for imparting proper weight distribution and balance to the user. Similarly, and as shown in FIG. 2, one or more discs 16 may be deployed on the plate and/or the heel cup portion of the orthotic 10 to provide the necessary adjustment for a particular user. For example, one disc 16 may be deployed on the posterior portion and one or more discs 16', 16", etc., on the anterior portion. The locations and orientations of discs 16 on a given plate 12 and/or heel cup portion are determined on a case-by-case basis by a skilled practitioner, based on the balancing needs of an individual user. The disc 16 may, likewise, have any suitable diameter as dictated by the orthotic device 10 and/or post 14 to which it is to be secured. Similarly, in a commercial form, the present disc 16 may be packaged as a kit wherein a pluality of discs have varying angles of inclination between the prescribed ranges.

As noted hereinabove, the present disc may be disposed directly on a footwear item, also, by placing it inside a shoe, sandal, etc., at the appropriate position or on a planar insole.

Further, the present device or disc may be used in conjunction with a biomechanical device such as an ankle brace, a foot brace, a combined ankle and foot brace and the like, where stabilization of the heel is required. The device hereof may be directly incorporated into such a brace with provision for access thereto for adjustment being provided, or may be used as a separate element in conjunction therewith.

While the invention has been illustrated and described in detail in the drawings and the foregoing description, the same is to be considered as illustrative and not restrictive in character, it being understood that only the preferred embodiment has been shown and described fully and that all changes and modifications that come within the spirit of the invention are desired to be protected.

Having, thus, described the invention what is claimed is:

1. A kit of discs, the discs for balancing the gait of a user, the kit comprising:

a plurality of the discs, each disc comprising a substantially rigid, circular wedge member having an planar upper surface and a planar lower surface, the upper and lower surfaces being angularly inclined with respect to each other by an angle of about 2° to about 6°, the disc being attachable to a footwear item and being rotatable through a 360° arc to enable incremental balancing adjustment for imparting proper weight distribution and balance to the user, and wherein the discs have varying angles of inclination.

2. The balancing disc of claim 1 wherein the discs are formed of a solid material which is either a rigid foam, steel, or plastic.

* * * * *